United States Patent
Reichenbach et al.

(10) Patent No.: US 7,564,033 B2
(45) Date of Patent: Jul. 21, 2009

(54) MICROSTRUCTURED SENSOR

(75) Inventors: Frank Reichenbach, Wannweil (DE); Holger Hoefer, Sonnenbuehl (DE)

(73) Assignee: Robert Bosch GmbH, Stuttgart (DE)

(*) Notice: Subject to any disclaimer, the term of this patent is extended or adjusted under 35 U.S.C. 154(b) by 373 days.

(21) Appl. No.: 10/563,993

(22) PCT Filed: Jan. 14, 2005

(86) PCT No.: PCT/DE2005/000040
§ 371 (c)(1), (2), (4) Date: Jan. 6, 2006

(87) PCT Pub. No.: WO2005/085808
PCT Pub. Date: Sep. 15, 2005

(65) Prior Publication Data
US 2008/0053254 A1 Mar. 6, 2008

(30) Foreign Application Priority Data
Mar. 4, 2004 (DE) .................. 10 2004 010 499

(51) Int. Cl.
*G01N 21/00* (2006.01)
*G01J 5/04* (2006.01)
*G01P 15/00* (2006.01)

(52) U.S. Cl. .............. 250/338.5; 250/343; 250/339.13; 438/64; 73/431; 73/488

(58) Field of Classification Search .......... 436/51, 436/55, 64, 112, 123; 257/433, 434; 250/338.1–338.05, 250/339.01, 339.02, 343, 339.11–339.13; 73/31.05, 431, 488; 438/51, 64
See application file for complete search history.

(56) References Cited

U.S. PATENT DOCUMENTS
4,021,766 A * 5/1977 Aine .................. 338/2

(Continued)

FOREIGN PATENT DOCUMENTS
DE 102 43 014 3/2004

(Continued)

OTHER PUBLICATIONS

G. R. Lahiji and K. D. Wise, "A batch-fabricated Silicon Thermoplie Infrared Detector", IEEE Transactions on Electron Devices, vol. ED-29, No. 1, 1982.*

*Primary Examiner*—Lisa M Caputo
*Assistant Examiner*—Punam Patel
(74) *Attorney, Agent, or Firm*—Kenyon & Kenyon LLP

(57) ABSTRACT

The invention relates to a microstructured sensor, having at least one measurement chip in which there is formed a first measurement area having a first measurement structure and a second measurement area having a second measurement structure, the measurement areas being offset to one another in a lateral direction, one cap chip that is fastened in vacuum-tight fashion to the measurement chip in a connecting area, one intermediate space, formed between the measurement chip and the cap chip, that is sealed outwardly by the connecting area and in which the measurement areas are situated, and at least one contact area, formed on the measurement chip, and left exposed by the cap chip, for the contacting of the measurement chip. The sensor can be in particular a gas sensor for measuring a gas concentration, or an acceleration sensor.

10 Claims, 3 Drawing Sheets

U.S. PATENT DOCUMENTS

| | | | |
|---|---|---|---|
| 5,521,123 A * | 5/1996 | Komatsu et al. | 438/64 |
| 5,584,117 A * | 12/1996 | Lee et al. | 29/620 |
| 5,668,033 A | 9/1997 | Ohara et al. | |
| 5,729,019 A * | 3/1998 | Krafthefer et al. | 250/353 |
| 5,841,137 A * | 11/1998 | Whitney | 250/338.5 |
| 5,962,854 A * | 10/1999 | Endo | 250/349 |
| 6,252,229 B1 | 6/2001 | Hays et al. | |
| 6,652,452 B1 * | 11/2003 | Seifert et al. | 600/140 |
| 7,402,453 B2 * | 7/2008 | Derderian et al. | 438/64 |
| 2002/0139410 A1 | 10/2002 | Wilner et al. | |
| 2006/0016995 A1 * | 1/2006 | Kummer et al. | 250/338.1 |
| 2006/0063292 A1 * | 3/2006 | Landsberger | 438/51 |
| 2008/0061237 A1 * | 3/2008 | Franz et al. | 250/338.1 |

FOREIGN PATENT DOCUMENTS

| | | |
|---|---|---|
| EP | 1 079 220 | 2/2001 |
| WO | WO 2004114403 A1 * | 12/2004 |

* cited by examiner

MICROSTRUCTURED SENSOR

FIELD OF THE INVENTION

The invention relates to a microstructured sensor that can be in particular a gas sensor or acceleration sensor, and a method for its manufacture.

DESCRIPTION OF RELATED ART

Some sensors have, in addition to a measurement channel, a reference channel for carrying out two measurements in parallel or that are carried out under different conditions. In gas sensors having a reference channel, two separate chips, generally of different wafers, are mounted in a housing. Such gas sensors generally have a membrane having an undercut cavity. However, the internal pressure of the sensor, or the cavity internal pressure, as well as additional parameters such as doping and cavity depth, can deviate significantly from one another in the different sensors, so that different measurement characteristics, and therefore high degrees of imprecision, can result in the comparison of the measurements of gas sensors. Also, the manufacturing of two sensors and their placement in a housing result in correspondingly high manufacturing costs.

In addition, acceleration sensors are known in which to measurement structures operated in parallel are formed on one chip. The contacting takes place through contact pads or outer terminals on one side of the chip. Given a more expensive connection of the sensor in a housing, the contacting to the conductive frame or lead frame of the housing may be expensive.

SUMMARY OF THE INVENTION

The sensor and method of manufacturing a sensor according to the invention has the advantage of rendering possible a high degree of spatial integration of measurement structures. According to the invention, both measurement structures are formed on one chip and are accommodated in a common intermediate space under a cap. Very good synchronization characteristics are achieved through the spatial proximity, the identical gas content, and in particular also the identical internal pressure, as well as the direct thermal coupling via the cap and substrate of the measurement chip.

Here, a multi-sided situation of the contact areas advantageously enables a better use of the contact pins of the packing housing. In principle, according to the present invention for example a one-sided formation of a larger contact area is also possible, which for example would have to be contacted to three sides.

BRIEF DESCRIPTION OF THE DRAWINGS

The present invention will be described in greater detail with reference to the following drawings wherein.

DETAILED DESCRIPTION OF THE INVENTION

The sensor according to the present invention can be in particular a gas sensor that detects infrared radiation in a measurement wavelength range and a reference wavelength range. Through the absorption of infrared radiation in particular wavelength range is, the concentration of individual gases in a gas mixture, e.g. of $CO_2$ in the ambient air, can be determined. Such a gas sensor can be used for example to determine the air quality in the passenger compartment of a passenger vehicle, as well as to determine leakages in a climate control system that uses $CO_2$ coolant. In addition, selective gas measurements for other gases and applications are also possible. The sensor according to the present invention has at least to measurement areas formed on a chip that are situated in a common intermediate space under a common cap chip. In principle, it is also possible for more than to measurement areas to be provided. The measurement conditions are very well matched due to the direct thermal coupling between the measurement areas via the substrate and the common cap, as well as by the identical gas content in the intermediate space.

The design according to the present invention, having two measurement areas on one chip and only one cap, also offers cost advantages during manufacture in comparison with the separate manufacture of two sensors. In addition, only one chip need be placed and contacted in a sensor module.

In the placement in a housing, both a chip-on-chip and also a flip-chip technique can be used, in which the measurement chip is placed on an evaluation chip. Here a high degree of efficiency in the use of space can be ensured, because the external terminals can be distributed uniformly, so that the wiring expense on the evaluation chip is lower.

In larger sensors in particular, a way for bonding support point can be formed in the intermediate space between the to measurement areas, so that the gas sensor can be exposed to hire loads. Thus, the sensor can in particular also subsequently be housed in a molded housing without being dented by the pressures that occur during molding.

Figure 1:
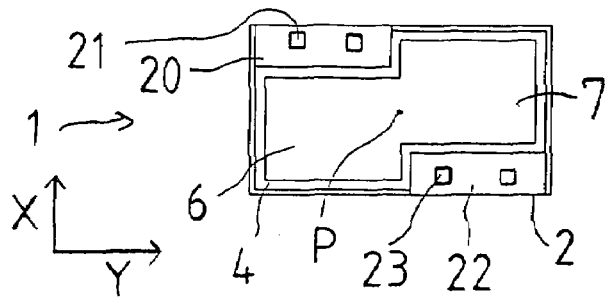
FIG. 1 shows a top view of a chip system of a gas sensor according to a first specific embodiment, having measurement areas rotated by 180° to one another and having contact areas on two sides.

According to FIG. 1, a gas sensor 1 has a measurement chip 2 made of silicon and a cap chip 4 that is made of silicon and is fastened on measurement chip 2 in a connection area 3. Between cap chip 4 and measurement chip 2, according to the vertical section seen in FIG. 6 an intermediate space 5 is formed that is sealed in vacuum-type fashion against the external space by connecting area 3 between measurement chip 2 and cap chip 4. Connecting area 3 can in particular be formed by a sealing glass connection, having for example a lead glass with a low melting point.

On measurement chip 2, two measurement areas 6, 7 are formed in a lateral direction Y so as to be offset from one another, e.g. directly adjoining one another; in this specific embodiment these measurement areas are also offset somewhat to one another in a longitudinal direction X that runs orthogonal to the lateral direction Y. measurement areas 6, 7 can in particular be formed for the measurement of infrared radiation in various wavelength range is, or for the measurement of accelerations, e.g., an identical acceleration in a first measurement and in a second measurement acting as a reference.

Figure 6:
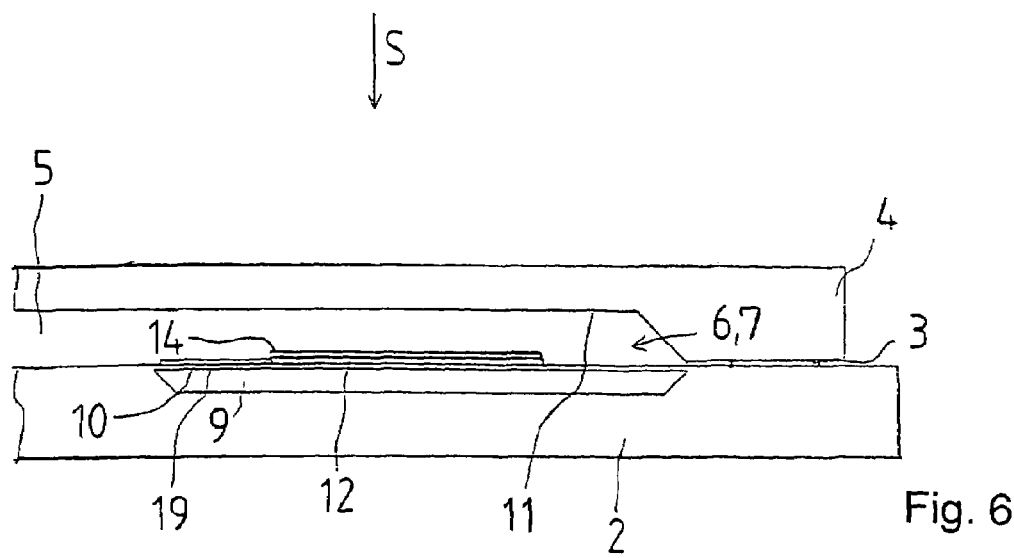
FIG. 6 shows a section through an exemplary measurement structure.

According to the specific embodiment as an infrared sensor or gas sensor according to FIG. 6, each measurement area 6 or 7 is formed through microstructuring of measurement chip 2, and has in a known manner, according to FIG. 6, a membrane 10 undercut through a cavity 9, a thermal pile structure 12 formed on membrane 10 and made up of two contacted (e.g. overlapping) printed conductors made of differently conductive materials, e.g. a metal and polysilicon, as well as an absorber layer 14 applied on thermal pile structure 12.

Cap chip 4 has on its underside an etched recess 11 for the forming of intermediate space 5. On cap chip 4, above measurement areas 6, 7 radiation filters can be attached using glue that allow infrared radiation S to pass only in predetermined wavelength range is; alternatively, such radiation filters can also be provided at different locations in the optical beam path.

In each of measurement areas 6, 7 infrared radiation S that is to be detected exits through cap chip 4, which is made of silicon that is transparent to the infrared radiation S, and through intermediate space 5, and comes into contact with absorber layer 14, which is heated thereby dependent on the intensity of the radiation. In this way, a thermovoltage is produced at thermopile structure 12 that can be read out electrically. For this purpose, printed conductors 19 run from thermopile structure 12 of measurement areas 6, 7 to contact areas 20, 22, which are subsequent in longitudinal direction X and which have terminal pads 21, 23 for contacting gas sensor 1.

The radiation filters provided in the optical beam path allowed infrared radiation to pass in predetermined different wavelength ranges in order to enable a quantitative measurement of the composition of a gas. Through the reference measurement of second measurement area 7, the measurement of first measurement area 6 can be normed or corrected.

Contact areas 20, 22 of measurement chip 2 are not covered by cap chips 4, and can thus be contacted with wire bonds.

In the specific embodiment of FIG. 1, contact areas 20, 22 are offset to one another in the lateral direction Y, and are provided at sides situated opposite one another in longitudinal direction X; i.e., measurement areas 6, 7 and contact areas 20, 22 are rotated to one another by 180° about a central point of symmetry P, or are situated symmetrically in relation to this point.

Figure 2:
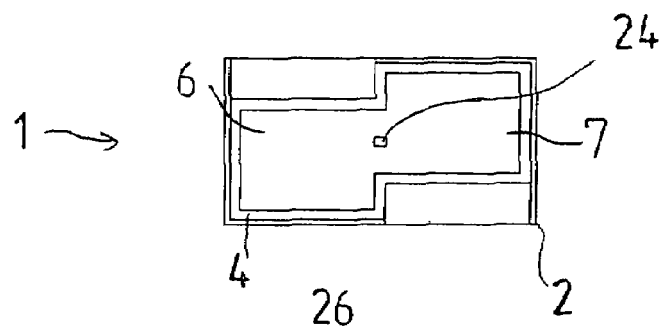
FIG. 2 shows a top view of a gas sensor according to another specific embodiment, having, in contrast to FIG. 1, an additional wafer bonding support point in the center of the chips.

The specific embodiment of FIG. 2 differs from that of FIG. 1 in particular in that in the center of measurement chip 2 a wafer bond support point 24 is formed on which cap chip 4 is supported on measurement chip 2. For this purpose, cap chip 4 can have for example a web protruding downward; that is, no recess 11 is formed in cap chip 4 in the area of wafer bond support point 24. Wafer bond support point 24 can for example be formed by a sealing glass connection, corresponding to that of connecting area 3. The additional wafer bond support point 24 increases the stability of gas sensor 1 against loads from above.

Figure 3:
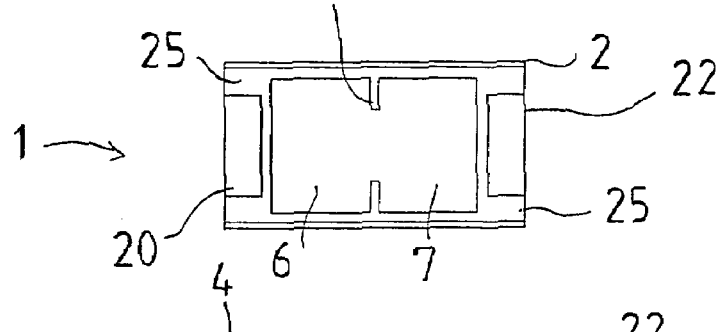
FIG. 3 shows a top view of a chip system of a sensor having contact areas on two opposing sides and having an interrupted centrally situated wafer bonding support point.

In the specific embodiment of FIG. 3, measurement areas 6, 7 are situated adjacent to one another in the lateral direction Y. Contact areas 20, 22 are situated on sides of measurement chip 2 situated opposite one another in the lateral direction, and are again recessed from cap chip 4. In this specific embodiment, auxiliary structures 25 for the cap processing are formed before and after contact areas 20, 22 in longitudinal direction X, as parts of connecting area 3; the same holds correspondingly in FIGS. 4a and 5. In the specific embodiment of FIG. 3, in the center of measurement chip 2 an interrupted wafer bond support point 26 is formed between measurement areas 6, 7 in order to increase the stability of gas sensor 1. Wafer bond support points 24, 26 of FIGS. 2, 3 do not, however, partition the entire intermediate space 5 of measurement areas 6, 7, so that a gas exchange is still possible. In the specific embodiment of FIG. 4a, in contrast to that of FIG. 3, interrupted wafer bond support point 26 is omitted, but wafer bond support points are possible here as well.

Figure 4A:
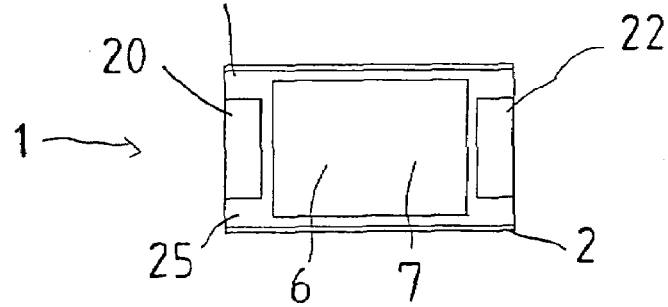
FIG. 4a shows a top view of a chip system of a gas sensor according to another specific embodiment, having contact areas on two opposite sides and having auxiliary structures for the cap processing at the edge of the chip.
Figure 4B:
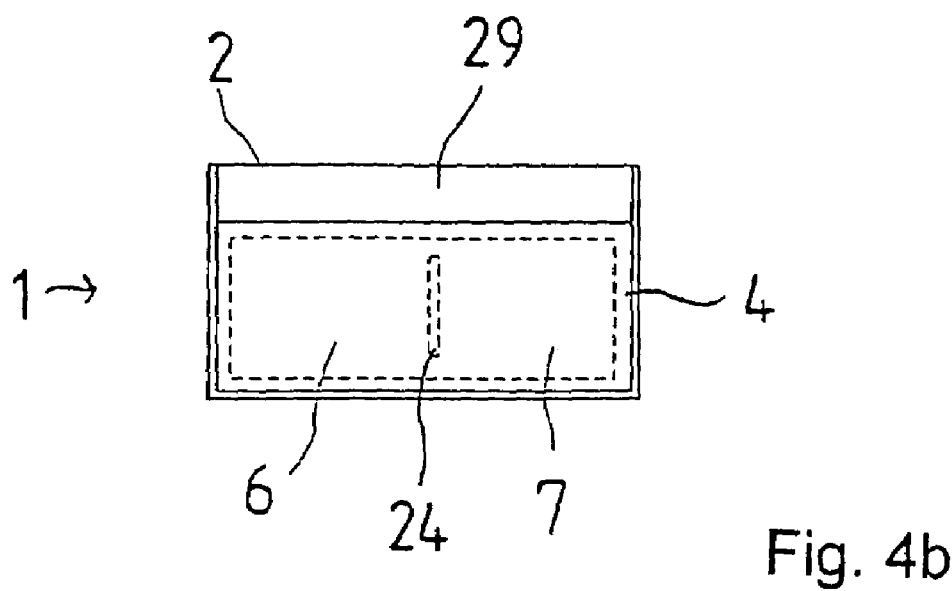
FIG. 4b shows a top view of a chip system of a gas sensor according to another specific embodiment, having a large contact area on one side, a wafer bonding support point as an optical separation, and a common cap recess.

FIG. 4b shows a specific embodiment in which measurement areas 6 and 7 are offset in the lateral direction and a wafer bond support point 24 acts as an optical separation. A contact area 29 is left open by cap chip 4 on only one side of measurement chip 2. Contact area 29 can here also be partitioned.

Figure 5:
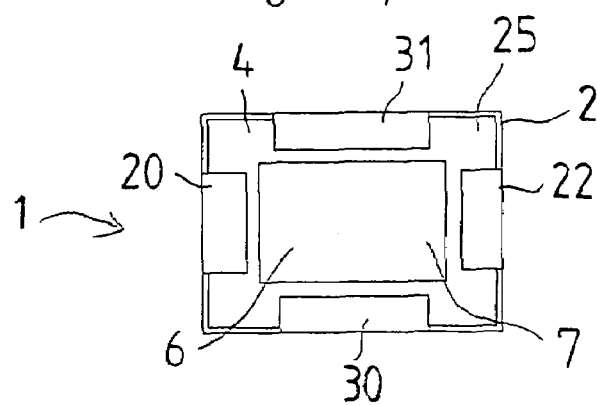
FIG. 5 shows a top view of a chip system of a gas sensor according to another specific embodiment having measurement areas situated opposite one another, contact areas on for sides, and auxiliary structures for cap processing on the edge of the chip.

FIG. 5 shows a specific embodiment of gas sensor 1 in which a contact area 30, 31 is also provided on each of the two additional outer edges situated opposite one another in the longitudinal direction and is recessed from cap chip 4. In this way, measurement chip 2 can be contacted on all four sides. In this specific embodiment as well, the auxiliary structures 25 described in relation to FIGS. 3, 4a are formed as parts of connecting area 3 for the cap processing in the isolation of the individual gas sensors 1.

Measurement areas 6, 7 of the specific embodiment of FIGS. 1 to 5 correspond in their design to the representation shown in FIG. 6.

The manufacture of gas sensors 1 of FIGS. 1 to 5 can take place on the wafer plane before the separation, and is thus economical on a large scale. For this purpose, first measurement areas 6, 7 are structured on a measurement wafer in a known manner. In addition, on a cap wafer a structuring is carried out in order to form the later cap chip 4, in which contact areas 20, 22 are recessed by etching and recesses 11 are formed in the lower side for intermediate spaces 5. Subsequently, the measurement wafer and the cap wafer are fitted to one another and, by means of sealing glass, connecting areas 3, as well as possible wafer bond support points 24, 26, are formed. Subsequently, gas sensors 1 can be manufactured by separation, i.e., sawing of the formed wafer stack.

Figure 7:
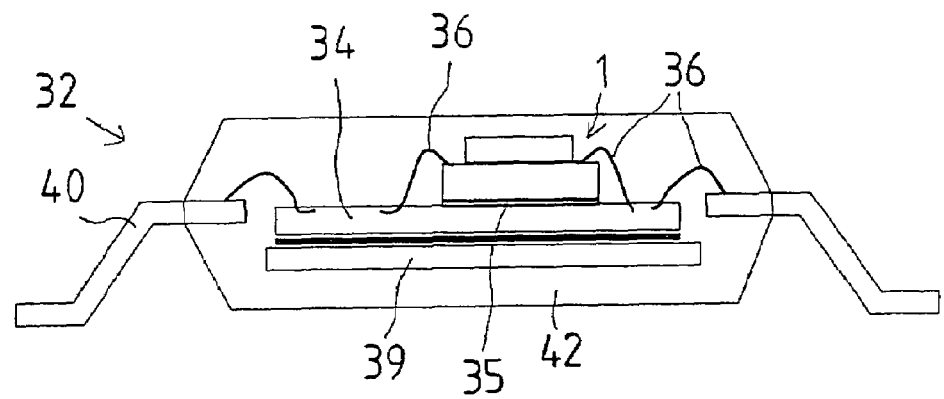
FIG. 7 shows a vertical section through a sensor module according to a specific embodiment of the present invention, having a sensor placed on an evaluation chip in a molded housing.
Figure 8:
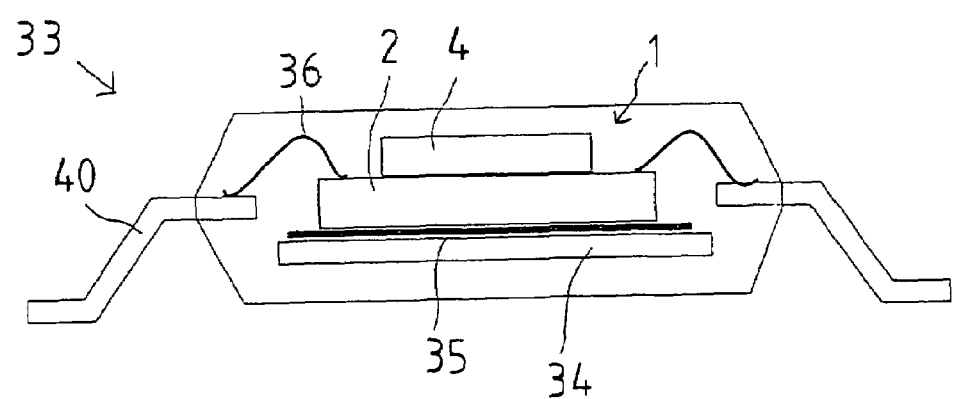
FIG. 8 shows a vertical section through a sensor module according to another specific embodiment, having a gas sensor that is contacted with a lead frame and is molded into a housing.

Gas sensor 1 according to the present invention can be housed in various types of packings. In FIGS. 7, 8, sensor modules 32, 33 having molded housings are shown as possible specific embodiments. Alternatively, however, it is in principle also possible to use e.g. a pre-molded housing to which a cover is fitted, or a ceramic housing.

In sensor module 32 of FIG. 7, gas sensor 1 is placed on an ASIC (application specified integrated circuit) 34, e.g. by gluing using an adhesive later 35, or by soldering. Terminal pads 21 of gas sensor 1 are contacted to ASIC 34 via wire bonds 36. ASIC 34 is in turn placed on a diepad 39. In addition, a lead frame 40 having individual contact pins is provided that is contacted with ASIC 34 via wire bonds 36.

This system is molded or injected into a housing 42 made of plastic or of a molding compound. For the manufacturing, for example each gas sensor 1 can be placed on an ASIC 34 and can be contacted to it via wire bonds 36. ASICs 34 are subsequently placed onto diepads 39 of a lead frame structure made up of a plurality of contiguous lead frames 40; housing 42 is subsequently molded, and the individual sensor modules 32 are then separated by cutting the lead frame structure.

In the specific embodiment of FIG. 8, gas sensor 1 is fastened directly to a diepad 39 for example by means of an adhesive layer 35. Terminal pads 21 of gas sensor 1 are contacted to lead frame 40 via wire bonds, and this system is molded into a housing 42 made of molding compound or plastic.

In the specific embodiment of FIG. 7, 8, an evaluation of the measurement signals of gas sensor 1 can be carried out directly in ASIC 34. In principle, however, it is also possible to form an integrated circuit in measurement chip 2 for the evaluation of the measurement signals.

What is claimed is:

1. A microstructured sensor, comprising:
   one measurement chip in which there is formed a first measurement area having a first measurement structure and at least one second measurement area having a second measurement structure, the measurement areas being offset to one another in a lateral direction;
   one cap chip that is made of silicon and is fastened in vacuum-tight fashion to the measurement chip in a connecting area;
   one intermediate space, formed between the measurement chip and the cap chip, that is sealed outwardly by the connecting area and in which the measurement areas are situated; and
   at least one contact area, formed on the measurement chip, and left exposed by the cap chip, for the contacting of the measurement chip, wherein between the measurement areas there is formed a wafer bond support point in which the cap chip is fastened on the measurement chip;
   wherein the microstructured sensor is a gas sensor for measuring a gas concentration, the first measurement area is provided for the detection of incident infrared radiation in a first wavelength range, the second measurement area is provided for the measurement of infrared radiation in a second wavelength range, and the cap chip is transparent to the infrared radiation that is to be measured.

2. The microstructured sensor according to claim 1, further comprising:
   at least two contact areas on the measurement chip, formed on different sides of the measurement chip and left exposed by the cap chip, for the contacting of the measurement chip.

3. The microstructured sensor according to claim 2, wherein the measurement areas and the contact areas are essentially offset to one another by 180° in relation to a point of symmetry of the measurement chip.

4. The microstructured sensor according to claim 2, wherein the contact areas are formed on sides situated opposite one another in a longitudinal direction, and are situated so as to be offset to one another in the lateral direction.

5. The microstructured sensor according to claim 2, wherein the contact areas are formed on the sides of the measurement chip situated opposite one another in the lateral direction.

6. The microstructured sensor according to claim 2, wherein the measurement areas are situated adjacent to one another in the lateral direction, and at least one contact area is formed on each of the four sides of the measurement chip.

7. The microstructured sensor according to claim 1, wherein the measurement structures each have a membrane undercut with a cavity, a thermopile structure formed on the membrane, and an absorber layer applied on the thermopile structure.

8. The microstructured sensor according to claim 1, wherein the wafer bond support point is interrupted.

9. The microstructured sensor according to claim 1, wherein the cap chip covers the measurement chip essentially completely except for the contact areas.

10. A sensor module, comprising:
    a microstructured sensor, including:
      one measurement chip in which there is formed a first measurement area having a first measurement structure and at least one second measurement area having a second measurement structure, the measurement areas being offset to one another in a lateral direction;
      one cap chip that is made of silicon and is fastened in vacuum-tight fashion to the measurement chip in a connecting area;
      one intermediate space, formed between the measurement chip and the cap chip, that is sealed outwardly by the connecting area and in which the measurement areas are situated; and
      at least one contact area, formed on the measurement chip, and left exposed by the cap chip, for the contacting of the measurement chip, wherein between the measurement areas there is formed a wafer bond support point in which the cap chip is fastened on the measurement chip;
    a lead frame; and
    a housing that surrounds a part of the lead frame and the microstructured sensor, wire bonds running from the at least one contact area of the measurement chip of the microstructured sensor in various directions to the lead frame;
    wherein the microstructured sensor is fastened and contacted on an evaluation chip that is contacted to the lead frame.

* * * * *